United States Patent [19]

Coffey

[11] Patent Number: 5,529,667
[45] Date of Patent: Jun. 25, 1996

[54] PROCESS FOR RECOVERING ETHYLENE OXIDE

[75] Inventor: Freylon B. Coffey, Corpus Christi, Tex.

[73] Assignee: Hoechst Celanese Corporation, Somerville, N.J.

[21] Appl. No.: 347,622

[22] Filed: Dec. 1, 1994

[51] Int. Cl.⁶ ........................................ B01D 3/38
[52] U.S. Cl. ................... 203/96; 203/76; 203/92; 203/93; 203/97; 203/DIG. 25
[58] Field of Search ................... 203/96, 97, 76, 203/92, 93, DIG. 19, DIG. 25, 49; 549/541

[56] References Cited

U.S. PATENT DOCUMENTS

| | | | |
|---|---|---|---|
| 3,165,539 | 1/1965 | Lutz | 549/541 |
| 3,418,338 | 12/1968 | Gilman et al. | 549/541 |
| 3,745,092 | 7/1973 | Vanderwater | 549/541 |
| 3,964,980 | 6/1976 | Ozero | 203/96 |
| 4,134,797 | 1/1979 | Ozero | 549/541 |
| 4,966,657 | 10/1990 | Delannoy et al. | 549/541 |

*Primary Examiner*—Robert J. Warden
*Assistant Examiner*—Krisanne M. Thornton
*Attorney, Agent, or Firm*—Donald R. Cassady

[57] ABSTRACT

In an improved process for recovering ethylene oxide from an aqueous ethylene oxide solution further containing formaldehyde is provided wherein the impure aqueous ethylene oxide solution is introduced into a distillation zone as a feed stream and undergoes distillation therein to form an ethylene oxide product sidestream and an aqueous bottoms product, water is added to the distillation zone to absorb formaldehyde vapor into a liquid phase and combines with the formaldehyde vapor to form an apparent azeotrope, and removing the apparent azeotrope from the column, the improvement is that all or part of the water is a recycled aqueous stream originating from the aqueous bottoms product and introduced to the distillation zone above the feed stream.

29 Claims, 3 Drawing Sheets

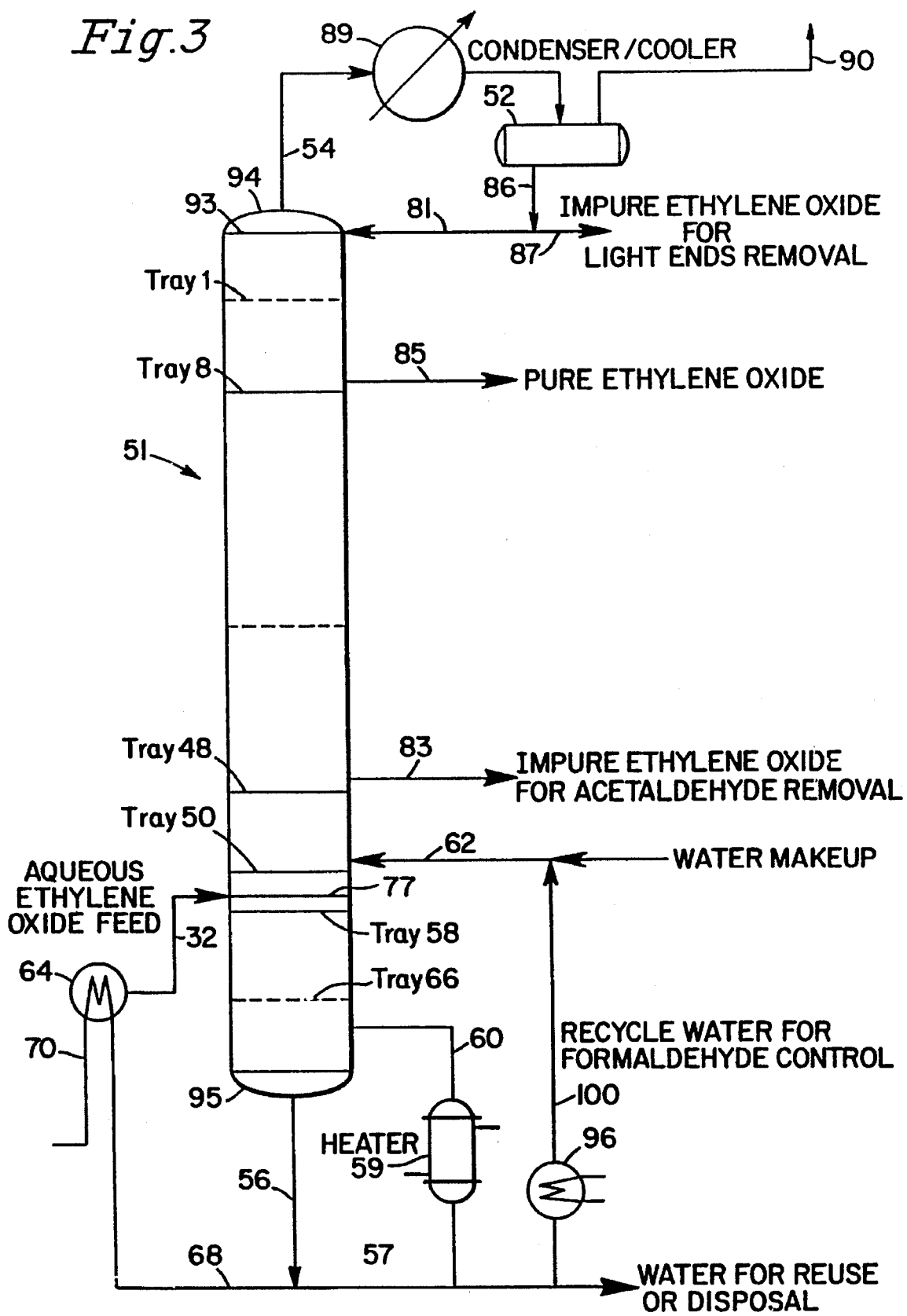

PROCESS FOR RECOVERING ETHYLENE OXIDE

BACKGROUND OF THE INVENTION

This invention relates to a process for recovering ethylene oxide from aqueous solutions containing the same. More particularly, this invention relates to an improved process for recovering ethylene oxide from an impure aqueous solution further containing formaldehyde impurity and, optionally, acetaldehyde.

Ethylene oxide, a staple in commerce, is prepared by the industry in large quantities by oxidizing ethylene with air or elemental oxygen over a suitable catalyst, typically a silver-containing catalyst, at elevated temperature (100° C. to 500° C. is typical) and at superatmospheric pressure (2 to 25 atmospheres), e.g., by the process of U.S. Pat. No. 2,775,510.

The dilute ethylene oxide mixtures obtained from these reactions, which may be suitably conducted in fixed or fluid-bed reactors, are scrubbed in an adsorber with water to form an aqueous solution of ethylene oxide and to thereby separate the ethylene oxide from unreacted ethylene, oxygen and other gaseous components of the reaction mixture (e.g., carbon dioxide). The separated gaseous materials are generally recycled to the catalytic oxidation step. The aqueous ethylene oxide solution is withdrawn from the absorber and passed to a stripper, e.g., stripping column. In the stripper, generally steam is introduced, usually countercurrently to the ethylene oxide solution fed thereto, to remove ethylene oxide product as overhead. An aqueous stream containing small quantities of formaldehyde and ethylene oxide is withdrawn from the stripper as bottoms and is recirculated to the absorber for use in absorbing additional ethylene oxide.

The overhead product from the stripping column, containing $CO_2$, ethylene oxide, gaseous inerts and water vapor, is cooled to partially condense the ethylene oxide and water contained therein, and the resulting mixture of vapor and liquid is passed to an ethylene oxide reabsorber, in which the uncondensed ethylene oxide vapor is reabsorbed in water. A predominance of the carbon dioxide and gaseous inerts which remain unabsorbed are readily separated as gaseous overhead stream from this reabsorption step. An aqueous solution is thus obtained which contains the reabsorbed ethylene oxide and aldehydic impurities, such as formaldehyde and acetaldehyde, as well as dissolved carbon dioxide and other gaseous impurities. This aqueous solution must be further treated to provide the high purity ethylene oxide required by the industry. In the process of U.S. Pat. Nos. 3,165,539, 3,174,262, and 3,964,980, this aqueous stream is passed to a "refining column" in which ethylene oxide is recovered as overhead and an aqueous bottoms is withdrawn for recycle to the reabsorber. In some processes (e.g., U.S. Pat. No. 3,904,656), the ethylene oxide overhead from the refining column is further purified in a second distillation column to remove any remaining carbon dioxide as overhead, and ethylene oxide bottoms are obtained which are passed to a third distillation column wherein purified ethylene oxide product is recovered as overhead.

The presence of high amounts of formaldehyde in the ethylene oxide stream can be undesirable from a processing standpoint. For example, the typical process of removing formaldehyde as an overhead bleed in the purification step following reabsorption of the ethylene oxide from the stripping column has several disadvantages. If the formaldehyde concentration in the overhead bleed is high, a solid paraformaldehyde phase can form in the overhead system of the column which can result in blockage and erratic operation and can possibly require shutdown and cleanout. See, e.g., J. Frederic Walker, *Formaldehyde*, pgs. 140–163 (3d Ed. Reinhold Publishing Corp.).

For the reasons outlined above, it is desirable to reduce formaldehyde content in the ethylene oxide stream as much as possible. It is further desirable to reduce formaldehyde content in ethylene oxide streams in as economical manner as possible.

U.S. Pat. No. 3,418,338 teaches a method wherein formaldehyde-rich streams produced during ethylene oxide purification can be further treated to reduce formaldehyde content by extractive distillation. However, separation of formaldehyde to increase the purity of the ethylene oxide product stream without the use of further distillation would be advantageous from a cost standpoint.

U.S. Pat. No. 4,134,797 to Ozero discloses a process for recovering ethylene oxide from an impure aqueous solution containing aldehydic impurities, wherein the impure solution is treated in a multi-stage, countercurrent distillation zone to separate the aldehydic impurities, resulting in an acetaldehyde-containing ethylene oxide stream, an ethylene oxide stream substantially free of aldehydic impurities, and a formaldehyde-containing ethylene oxide stream.

The Ozero patent reports that the distillate formaldehyde, i.e., the formaldehyde-containing ethylene oxide stream produced in the process therein contains usually from about 1000 ppm to about 3000 ppm of formaldehyde (see, e.g., column 9, lines 5–6). The ethylene oxide product stream is said to contain generally less than about 20 ppm and usually less than about 5 ppm of formaldehyde (see, e.g., column 8, lines 53–54).

Because certain applications are adversely affected by formaldehyde levels exceeding about 10 ppm, it is continually desirable to provide improved ethylene oxide purification methods which lower formaldehyde content to 10 ppm or less.

In the Ozero process, as is typical, formaldehyde is removed during distillation by washing the column with fresh, i.e., "once-through", water, which combines with the formaldehyde to form an "azeotrope" system and is removed with the bottoms product. Although Ozero uses the term "azeotrope" to describe the product formed from the combination of water and formaldehyde, it appears more likely that the water and formaldehyde react to form methylene glycol and polyoxymethylenes which alter the vapor-liquid equilibrium more than the water-formaldehyde "azeotrope". The term "apparent azeotrope" as used herein refers to the products formed from the combination of water and formaldehyde, including methylene glycol and polyoxymethylenes.

The formaldehyde-removing method disclosed in Ozero uses a great deal of water and leads to undesirable waste disposal problems. It is therefore desirable to provide an ethylene oxide purification process using distillation which reduces the formaldehyde content in the light ends stream and in the ethylene oxide product stream and uses less water.

While the methods described hereinabove produce an ethylene oxide stream which is substantially free of water, carbon dioxide and dissolved inert gases, these methods do not economically reduce the concentration of aldehydic impurities such as formaldehyde and acetaldehyde present in the ethylene oxide sought to be purified.

Therefore, one object of the present invention is to provide an improved process for purifying ethylene oxide which results in lower formaldehyde levels in the ethylene oxide product (e.g., 10 ppm or less) and in the light ends stream.

Another object of the present invention is to provide an improved distillation process for purifying ethylene oxide which uses less water to reduce formaldehyde content in the light ends stream and ethylene oxide product stream to the same levels achieved using the greater amounts of water as presently used.

These and other objects are achieved in the present invention.

SUMMARY OF THE INVENTION

The present invention provides an improved process for recovering ethylene oxide from an impure aqueous ethylene oxide solution further containing formaldehyde and, optionally, acetaldehyde.

According to the broadest aspect of the process of this invention, wherein an impure aqueous ethylene oxide solution is introduced into a distillation zone as a feed stream and undergoes distillation therein to form an ethylene oxide product sidestream and an aqueous bottoms product, and water is added to the distillation zone to absorb formaldehyde vapor into a liquid phase and combine with formaldehyde, the improvement comprises that all or part of said water is a recycled aqueous stream originating from the aqueous bottoms product and introduced into the distillation zone above the feed stream.

A preferred embodiment of the process of this invention comprises the steps of:

(A) preheating the impure solution and then introducing the preheated impure solution to a multi-stage countercurrent distillation zone, said distillation zone having disposed therein in ascending order above said feed stream entry conduit the following fractionation regions:

(1) a first fractionation region having at least one vapor-liquid contacting stage;

(2) a second fractionation region having at least one vapor-liquid contacting stage;

(3) a third fractionation region having at least five vapor-liquid contacting stages; and (4) a fourth fractionation region situated above the feed stream entry conduit and having at least one vapor-liquid contacting stage;

said distillation zone further having disposed therein a fifth fractionation region, wherein said fifth fractionation region is situated below the feed stream entry conduit and has at least one vapor-liquid contacting stage; each of said fractionation regions having means for providing countercurrent contact between downflowing liquid and upwardly flowing vapor;

(B) introducing stripping vapor to said distillation zone at a point below said fifth fractionation region;

(C) withdrawing from the distillation zone as a first sidestream at least a portion of a liquid downflowing from said third fractionation region, said first sidestream comprising an acetaldehyde-containing ethylene oxide stream;

(D) withdrawing from the distillation zone as a second sidestream at least a portion of a liquid downflowing from said fourth fractionation region, said second sidestream comprising an ethylene oxide substantially free of aldehydic impurities;

(E) withdrawing from said distillation zone above said fourth fractionation region formaldehyde-containing vapor formed in said fourth fractionation region, condensing at least a portion of said withdrawn vapor and recycling at least a portion of the condensate so produced as liquid reflux to the distillation zone above said fourth fractionation region, the portion of said condensate not so recycled being withdrawn as an ethylene oxide stream containing minute amounts of formaldehyde and, in most cases, small amounts of nitrogen and carbon dioxide;

(F) withdrawing from the distillation zone as a bottom stream at least a portion of an aqueous bottoms product formed below the fifth fractionation region and comprising an aqueous solution substantially free of ethylene oxide;

(G) cooling said bottom stream to a temperature ranging from about 35° C. to about 60° C.;

(H) recycling said cooled bottom stream to the distillation zone above the feed stream entry conduit, where said cooled bottom stream absorbs formaldehyde vapor into a liquid phase and water present in said cooled bottom stream combines with the formaldehyde vapor to form an apparent azeotrope; and (I) removing said apparent azeotrope from said distillation zone.

In addition to reducing formaldehyde content and water consumption, the process of this invention results in rapid and efficient removal of aldehydic impurities, particularly, formaldehyde, and substantial savings in utility costs (e.g., heating and cooling expense) and capital equipment expense.

BRIEF DESCRIPTION OF THE DRAWINGS

FIG. 3 is an illustration of the distillation column used in the Example presented herein.

DETAILED DESCRIPTION OF THE INVENTION

A further understanding of this invention will be facilitated by reference to the drawings, wherein like numerals refer to the same or similar element.

Figure 1:
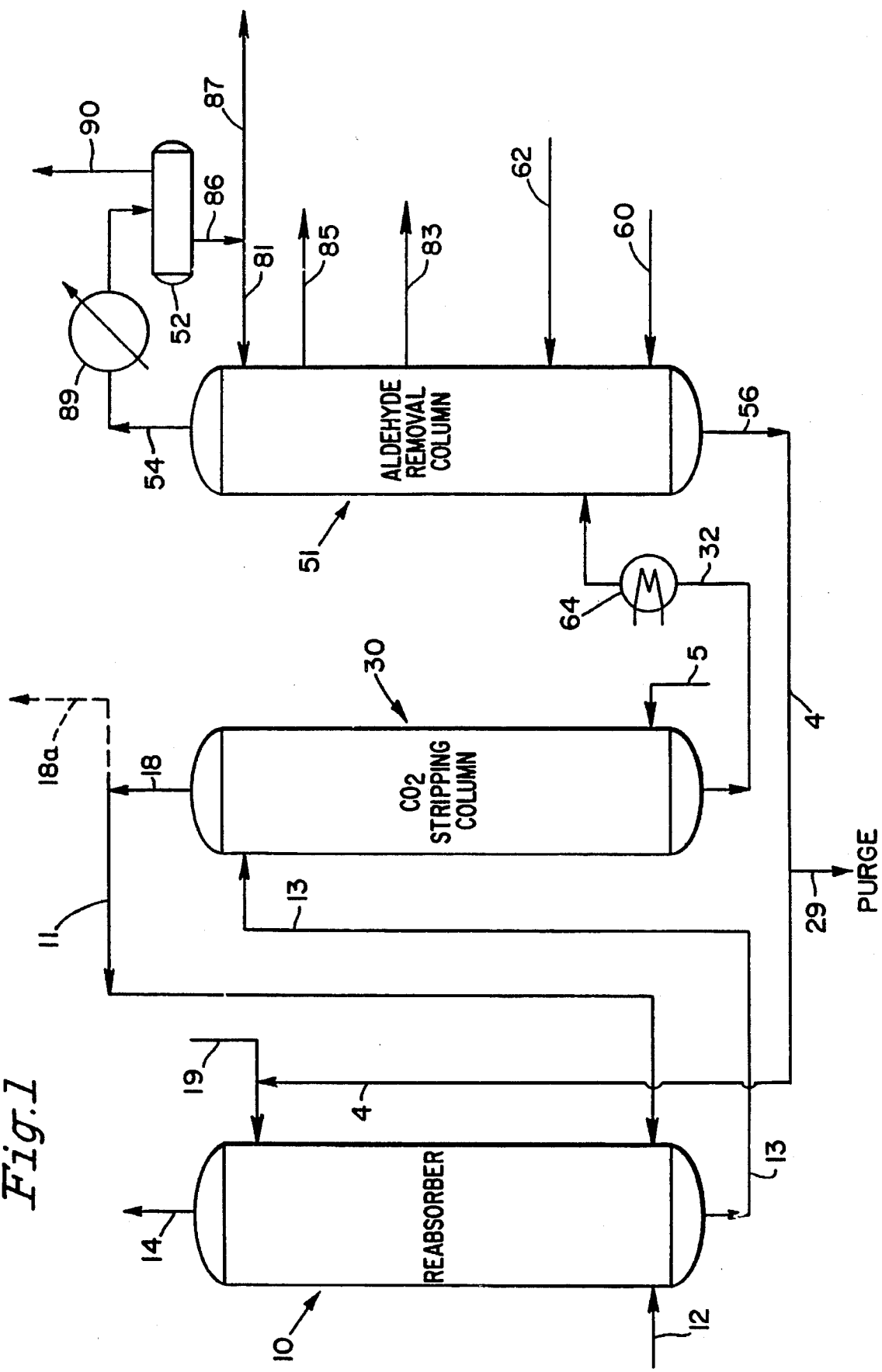
FIG. 1 is a diagrammatic illustration of the overall process for recovering high purity ethylene oxide incorporating the improved process of this invention.

In the overall process for recovering high purity ethylene oxide, as illustrated in FIG. 1, an ethylene oxide vapor stream containing carbon dioxide and formaldehyde impurity (and optionally acetaldehyde impurity) is passed via conduit 12 from a conventional stripper (not shown) to the lower portion of reabsorber 10 wherein the vapor stream is contacted in countercurrent fashion with an aqueous medium introduced to column 10 via conduit 19 to absorb ethylene oxide, thereby resulting in a reabsorbate which is withdrawn via conduit 13. Unabsorbed gases, including carbon dioxide, are withdrawn from the upper portion of column 10 via conduit 14. Bottoms withdrawn from column 10 via conduit 13 are passed to the upper portion of carbon dioxide stripping column 30 wherein the liquid is contacted, in countercurrent fashion, with stripping fluid such as steam (or other fluid such as $N_2$), to vaporize absorbed gases, including carbon dioxide, which are removed from the upper portion of column 30 and recycled to column 10 via conduit 11 for absorption of any residual ethylene oxide remaining in these gases. Unabsorbed gases such as carbon dioxide passing to column 10 via conduit 11 are withdrawn therefrom via conduit 14. Optionally, as where the ethylene oxide content of the gases passing from the upper portion of column 30 are sufficiently low (e.g., by use of a water wash step—not shown), the gases in conduit 18 can be vented directly. Bottoms withdrawn via conduit 32 from column 30 comprise an impure aqueous ethylene oxide solution which is then introduced as feed to column 51 for separation of water and aldehydic impurities therefrom, as will be more fully described below.

The operation of carbon dioxide stripping column 30 in the process depicted in FIG. 1 is entirely conventional, and a detailed description thereof is not necessary to a full understanding of the process of the present invention. Thus, column 30, for example, can comprise any suitably configured distillation column, whether packed bed or provided with distillation trays, and will generally posses from about 1 to 20, and more usually from about 5 to 10, minimum vapor-liquid contacting stages, and will generally employ a bottoms temperature of from about 20° C. to 100° C., and more usually from about 50° C. to 70° C., and an overhead pressure of from about 4 to 30 psia, usually from about 15 to 20 psia.

Figure 2:
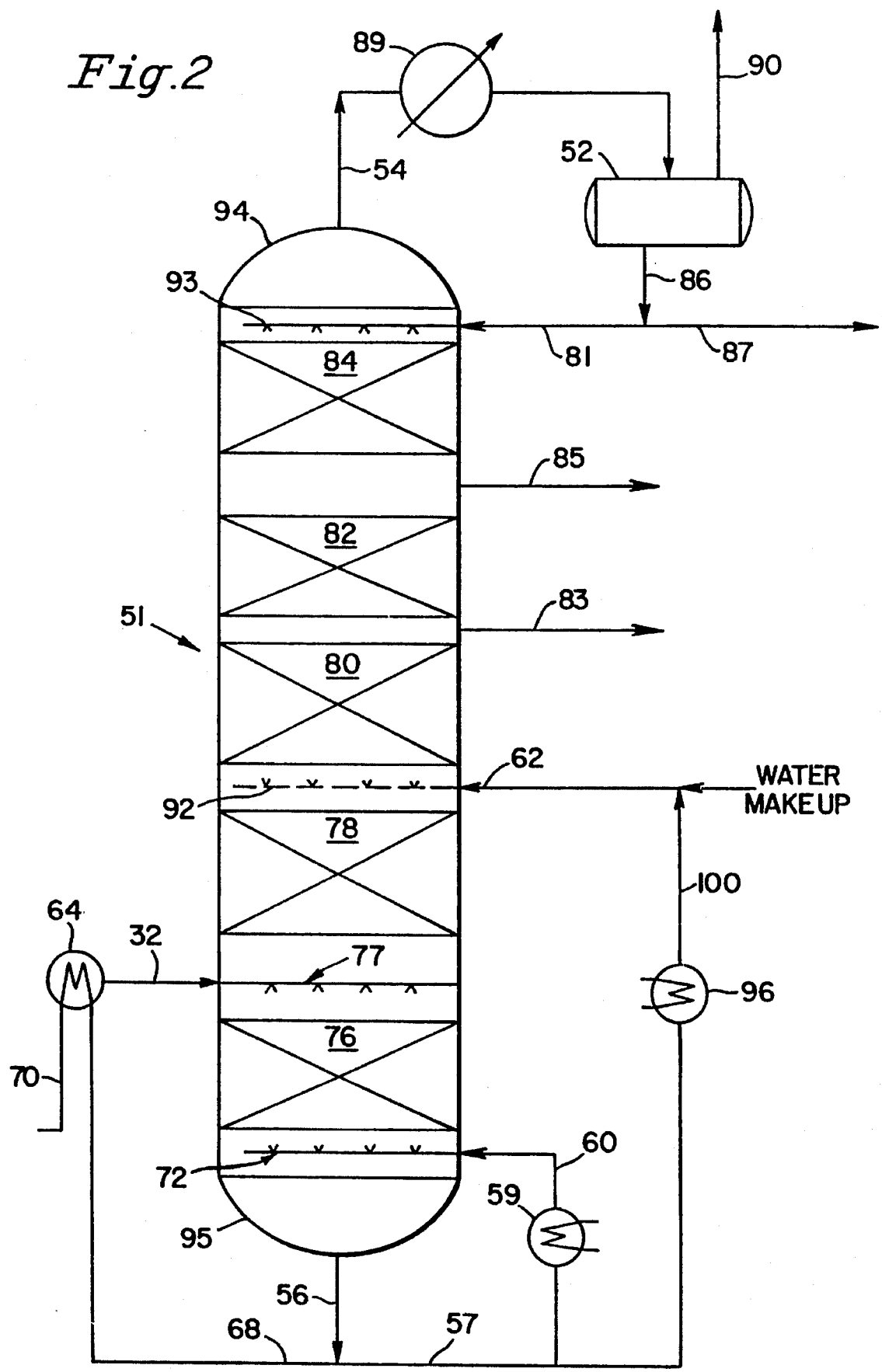
FIG. 2 is a diagrammatic illustration of an embodiment of the ethylene recovery process of the present invention which particularizes the aldehyde removal column used herein.

Referring to FIG. 2, the impure aqueous ethylene oxide solution, containing formaldehyde and, optionally, acetaldehyde impurities, is preheated by means of heat exchanger 64, typically to a temperature ranging from about 35° C. to about 120° C., preferably about 85° C., and the preheated solution is then passed via feed stream entry conduit 32 into a multi-stage distillation column, indicated generally at 51.

The composition of the impure aqueous ethylene oxide solution treated by the present invention for removal of formaldehyde impurity therefrom can vary widely. Generally, however, the impure liquid will contain from about 2 to about 90 weight percent, usually from about 40 to about 60 weight percent, ethylene oxide; from about 10 to about 98 weight percent, usually from about 40 to about 60 weight percent, water; and from about 0.001 to about 0.2 weight percent, usually from about 0.005 to about 0.05 weight percent, "aldehydic impurities," as the latter term is defined herein below. The impure liquid may also generally contain up to about 500 ppm by weight, usually up to about 250 ppm by weight, dissolved $CO_2$ (based on the ethylene oxide content of the impure liquid). The molar ratio of water to ethylene oxide in the impure liquid will generally be from about 1:1 to about 50:1, preferably from about 2:1 to about 30:1, and more preferably from about 2:1 to about 4:1.

The term "aldehydic impurities" as used herein is intended to refer to a member of the group consisting of formaldehyde, acetaldehyde and mixtures thereof. In the case of mixtures of aldehydic impurities, the relative amounts of such impurities are not critical to the present invention. Typically, the impure aqueous ethylene oxide solution will contain up to 0.1 weight percent, usually from 0.005 to 0.05 weight percent, formaldehyde, and from about 0.001 to 0.1 weight percent, usually from about 0.002 to 0.05 weight percent, acetaldehyde. However, impure ethylene oxide solutions containing formaldehyde and acetaldehyde outside the range of the foregoing molar ratio can also be treated by the present invention.

The impure aqueous ethylene oxide solution is introduced to column 51 via distributing member 77, which may comprise any of the conventional liquid or vapor distributor heads commonly used with such liquids.

In FIG. 2, column 51 is provided with the following fractionation regions, which are positioned in ascending order above feed stream entry conduit 32: first fractionation region 78 having at least one vapor-liquid contacting stage, preferably having from 1 to 20, and more preferably from 2 to 10, vapor-liquid contacting stages; second fractionation region 80 having at least one vapor-liquid contacting stage, preferably having from 1 to 15, and more preferably from 2 to 6, vapor-liquid contacting stages; third fractionation region 82 having at least 5 vapor-liquid contacting stages, preferably having from 10 to 60, and more preferably from 15 to 50, vapor-liquid contacting stages; and fourth fractionation region 84 having at least one vapor-liquid contacting stage, preferably having from 1 to 20, and more preferably from 2 to 10, vapor-liquid contacting stages. Fifth fractionation region 76, having at least one vapor-liquid contacting stage, and preferably having from 1 to 20, and more preferably from 3 to 12, vapor-liquid contacting stages, is provided within column 51 below feed stream entry conduit 32. Most preferably, first fractionation region 78 has from 4 to 7 vapor-liquid contacting stages, second fractionation region 80 has from 2 to 4 vapor-liquid contacting stages, third fractionation region 82 has from 25 to 40 vapor-liquid contacting stages, fourth fractionation region 84 has from 2 to 5 vapor-liquid contacting stages and fifth fractionation region 76 has from 4 to 8 vapor-liquid contacting stages.

The vapor-liquid contacting stages in column 51 shown in FIG. 2 can comprise any of the conventional distillation trays which are adapted for countercurrent vapor-liquid contacting and include sieve trays, bubble cap trays, valve trays, tunnel cap trays and the like. In addition one or more of the various fractionation regions within column 51 in FIG. 2 can comprise packings which are substantially inert to the components of the vapor and liquid contained in the column. Suitable packing therefore include Berle saddles, Raschig rings, Intalox saddles and the like. Both distillation trays and packed sections can be employed within the same column.

In the operation of column 51 as shown in FIG. 2, upwardly flowing vapors and downwardly flowing liquids are countercurrently contacted within each fractionation region. The liquid or vapor feed, which is preferably introduced to column 51 substantially uniformly across the diameter of the column, is at least partially vaporized therein.

The aqueous bottoms product collecting in the lower portion of column 51 comprises an aqueous solution containing generally less than about 0.1 weight percent, and preferably less than about 0.01 weight percent, ethylene oxide; generally less than about 0.1 weight percent formaldehyde; generally less than about 0.001 weight percent acetaldehyde; and generally from about 0.5 to 20 weight percent, preferably from about 1 to 5 weight percent, ethylene glycol; and is most preferably substantially free of ethylene oxide, that is, contains less than about 0.001 weight percent ethylene oxide. However, the precise composition can vary widely; for example, aqueous bottoms containing ethylene glycol in higher or lower concentrations can also be obtained. Ethylene oxide in bottoms product will generally move upwards in the column. Thus, the aqueous bottoms product which is withdrawn from the column will typically be substantially pure water. The aqueous bottoms product is withdrawn from column 51 via exit conduit 56.

As shown in FIG. 2, a portion of the aqueous bottoms product withdrawn as an aqueous bottom stream from column 51 via exit conduit 56 is passed through indirect contact heat exchanger 96 for cooling, and then reintroduced via conduits 57, 100 and 62 to column 51 above feed stream entry conduit 32, preferably between first fractionation region 78 and second fractionation region 80. Optionally, the aqueous bottom stream may be reintroduced to column 51 at a point above conduit 83 and below conduit 85. In the column, the aqueous bottom stream absorbs formaldehyde vapor into a liquid phase and the water present in the aqueous bottom stream combines with the formaldehyde vapor to form an apparent azeotrope. The apparent azeotrope, which, as stated previously herein, generally comprises methylene glycol and polyoxymethylenes, is relatively heavy and travels downward in column 51, where it is typically withdrawn from the column via conduit 56 and disposed via conduit 68. As stated previously herein, in current ethylene oxide purification processes using distillation, the water used to wash the column to remove formaldehyde is fresh, once-through water. In the present invention, the wash water may be composed of both fresh water and recycled aqueous bottoms liquid or may be composed entirely of the recycled liquid. Therefore, the present invention reduces the amount of fresh water used, or eliminates its use entirely, and still achieves the desired low levels of formaldehyde in the light ends stream and in the ethylene oxide product stream. The amount of-wash water to be used will depend on the amount of formaldehyde present in the feed stream and on the volume of the total feed flow. For example, from about 1 to about 300 gallons, preferably from about 10 to about 100 gallons, and most preferably from about 20 to about 30 gallons of water per minute, would typically be used when a feed stream containing 50% ethylene oxide and 50% by weight water is fed into the column at a rate of 300 gallons per minute.

To achieve maximum formaldehyde removal, the aqueous bottom stream is preferably cooled prior to its reentry into column 51. Typically, the aqueous bottom stream has a temperature of about 150° C. prior to cooling, this temperature being excessive for optimum formaldehyde removal. The aqueous bottom stream is generally cooled to a temperature ranging from about 35° C. to about 60° C., preferably about 55° C.

A second portion of the aqueous bottoms product withdrawn from column 51 via exit conduit 56 may be recycled via conduits 4 and 19 to column 10 for absorption of additional ethylene oxide. A purge is taken (via conduit 29) from the recycled bottoms in order to remove water and formaldehyde present in the feed to reabsorber 10 and glycol formed in preceding processing. While not critical to the present invention, the amount of such purge will generally range from about 0.1 to 25 weight percent, usually from 1 to 10 weight percent, of the bottoms product passed to line 4.

Stripping vapor, which can comprise steam or other suitable inert heating medium, is introduced via conduit 60 to column 51 below fifth fractionation region 76. Preferably, a portion of the withdrawn liquid bottoms is recycled via conduit 60 and reboiler 59 to column 51 to provide the necessary stripping vapor for operation of the column. The temperature of the liquid bottoms introduced to column 51 via conduit 60 is usually from about 130° C. to 160° C., and preferably from about 140° C. to 150° C. However, higher or lower temperature can also be used, with the particular temperature selected depending on a variety of factors obvious to the skilled practitioner, including liquid composition, column pressure and other factors.

Bottoms product in conduit 68 is passed to heat exchanger 64 to preheat the liquid feed contained in feed stream entry conduit 32. It is to be understood that conventional heat sources other than the bottoms product may be used to preheat the liquid feed. The cooled bottoms, which can be withdrawn from heat exchanger 64 via conduit 70, can then, after further cooling, be suitably recycled to a reabsorber for absorption of additional quantities of ethylene oxide. The relative amounts of withdrawn bottoms in exit conduit 56 which are passed to reboiler 59 or to heat exchanger 64 can be easily ascertained by the skilled practitioner and will vary widely depending on such factors as bottoms composition, the amount of heat to be imparted to column 51 via conduit 60.

The remaining portion of the withdrawn liquid bottoms which is not recycled to column 51 can be disposed via conduit 57 or passed to conduit 68, and after cooling can be suitably passed to a reabsorber (e.g., to column 10 via conduits 4 and 19 in FIG. 1) for absorption of additional quantities of ethylene oxide.

A portion of the liquid down-flowing from third fractionation region 82 is withdrawn from column 51 via conduit 83 and comprises an acetaldehyde-containing ethylene oxide stream. While the composition of this stream will vary widely, depending on such factors as the acetaldehyde content in the impure ethylene oxide feed introduced to column 51 via feed stream entry conduit 32, the temperature and pressure conditions employed in column 51 and other factors, it will generally contain at least about 88 weight percent, and preferably at least about 95 weight percent, ethylene oxide; generally from about 0.05 to 2 weight percent, usually from about 0.3 to 1 weight percent, water; and generally from about 0.1 to 10 weight percent, usually from about 0.2 to 2 weight percent, acetaldehyde, and is generally substantially free of formaldehyde. This acetaldehyde-containing ethylene oxide stream can be treated by conventional techniques to recover additional ethylene oxide, or can be fed to a process in which the acetaldehyde content of the ethylene oxide stream can be tolerated, e.g., in the hydrolysis of ethylene oxide to ethylene glycol by the process disclosed in U.S. Pat. No. 3,904,656.

A portion of the liquid down-flowing from fourth fractionation region 84 is withdrawn from column 51 via conduit 85 and comprises the desired ethylene oxide product containing the desired low concentrations of water and aldehydic impurities. While the precise composition of this ethylene oxide product will also vary depending on such factors as the temperature and pressure conditions in column 51, the number of vapor liquid contacting stages employed, the desired purity of the ethylene oxide product and other factors, the ethylene oxide product stream withdrawn via conduit 85 will be substantially free of aldehydic impurities and water, and will generally contain about 10 parts per million (ppm) or less, usually from about 2 ppm to about 5 ppm, of formaldehyde; generally about 58 ppm or less, usually from about 5 ppm to about 10 ppm, of acetaldehyde; and generally less than about 300 ppm, usually less than about 100 ppm, of water.

Vapors are withdrawn from the upper portion of column 51 via conduit 54 and passed to condenser 89, which may comprise a partial condenser. The effluent from condenser 89 is passed to vapor-liquid separator 52, from which liquid is withdrawn via conduit 86. A portion of this liquid, which comprises an ethylene oxide stream containing minute amounts of formaldehyde, is recycled via conduit 81 and distributing member 93 to column 51 above fourth fractionation region 84 as liquid reflux. The remaining condensate is withdrawn via conduit 87 and comprises the ethylene oxide stream containing minute amounts of formaldehyde. While the precise composition of the liquid withdrawn via conduit 87 may vary widely, the liquid will contain generally at least about 99.5 weight percent of ethylene oxide; and generally about 300 ppm or less, and usually about 50 ppm or less, of formaldehyde. This liquid will generally be substantially free of acetaldehyde, generally containing less than about 50 ppm acetaldehyde, and will also generally be substantially free of water, usually containing less than about 300 ppm of water. The ethylene oxide content of this formaldehyde-rich stream can vary widely, as is stated above, but will generally comprise up to about 25 weight percent, preferably up to about 15 weight percent, and most preferably up to about 10 weight percent, of the ethylene oxide fed to column 51 via impure ethylene oxide feed introduced through feed stream entry conduit 32.

The quantity of condensate recycled as reflux to column 51 via conduit 81, the quantity of liquid withdrawn as the formaldehyde-containing ethylene oxide stream via conduit 87, and the quantity of ethylene oxide product stream withdrawn via conduit 85 can vary widely. However, the most efficient operation, the internal liquid reflux ratio for column 51 should be at least about 1.35:1, and preferably from about 1.35:1 to 10:1, more preferably from about 3.5:1 to 7.5:1, and most preferably from about 4.0:1 to 6.0:1, wherein the internal liquid reflux ratio is defined by the following expression (I):

$$R = L/(P+F)$$

wherein "R" is the internal liquid reflux ratio, "L" is the moles per hour of liquid downflowing from the fourth fractionation region (i.e., zone 84 in FIG. 2) which is not withdrawn as the ethylene oxide product stream (i.e., not withdrawn via conduit 85 in the embodiments of FIG. 2), "P" is the moles per hour of liquid withdrawn as the ethylene oxide product stream (i.e., via conduit 85 in FIG. 2) and "F" is the moles per hour of liquid withdrawn as the formaldehyde-containing stream (i.e., via conduit 87 in FIG. 2).

The moles per hour of vapor and liquid streams referred to above with respect to expression (I) can be determined employing conventional techniques, and the rates of flow in these various streams to achieve the desired internal liquid reflux ratio can also be controlled by conventional methods, such as by positioning any suitable flow control valves in conduits 81 and 87, and a discussion here of such measurement techniques and flow control methods is not necessary to a full understanding of the present invention.

To the extent that additional quantities of formaldehyde and/or acetaldehyde can be tolerated in the ethylene oxide produced by this process, a portion of either the formaldehyde-containing stream or the acetaldehyde-containing stream, or both, can be admixed with the ethylene oxide product stream to obtain a resultant ethylene oxide-containing liquid stream having formaldehyde and acetaldehyde content not in excess of the maximum concentrations of these impurities which are desired. Alternatively, the formaldehyde-containing and acetaldehyde-containing streams withdrawn via conduits 87 and 83, respectively, can be further treated for removal of the formaldehyde and/or acetaldehyde content thereof (e.g., by extractive distillation employing the method of U.S. Pat. No. 3,418,338 for formaldehyde removal and distillation for acetaldehyde removal), or can be used directly as feed to a process in which the formaldehyde and acetaldehyde impurities may be tolerated, as for example in the production of ethylene glycol by hydrolysis of the ethylene oxide content of these purged streams.

Vapors formed in separator 52 can be withdrawn therefrom via conduit 90, and are preferably recycled to the feed conduit 12 of reabsorber 10, to avoid buildup in column 51 of carbon dioxide and other gaseous inerts introduced to column 51 via feed stream entry conduit 32.

Alternatively, or in addition, a portion or all of the formaldehyde-containing ethylene oxide stream in conduit 87 can be combined with the vapors in conduit 90 for recycle of such mixed stream to the reabsorber.

While the quantity of liquid in conduit 87 and vapors in conduit 90 can vary widely, generally, the total of the amount of liquid passed to conduit 87 via conduit 86 and vapors in conduit 90 will comprise from about 5 to 20 percent, and more preferably from about 5 to 10 percent, of the feed column 51 via feed stream entry conduit 32, based on the ethylene oxide content of the feed. Generally, vapors in conduit 90 will comprise less than about 10 percent by weight of the total amount of liquid and vapor passed to conduits 87 and 90.

The quantity of the ethylene oxide-containing formaldehyde stream recycled to either column 51 or reabsorber 10 is not critical to the present invention, and will be determined by economics of recovering additional quantities of ethylene oxide from the recycled stream.

The pressures employed in column 51 can vary widely and will of course depend on a variety of factors, such as the composition of the impure liquid feed, the temperatures selected for use in the column, the degree of removal of aldehydic impurities desired, and other factors, but will generally be from about 25 to 100 psig, usually from about 35 to 60 psig. However, higher or lower pressures can also be used.

Although FIGS. 1 and 2 only show the use of one distillation column, two or more side-by-side distillation columns, for example, as shown in FIG. 6 in U.S. Pat. No. 4,134,797, hereby incorporated by reference herein in its entirety, can be used in the process of this invention.

The invention will be more fully understood by reference to the following specific example, but it is to be understood that this example is given solely for illustrative purposes and is not intended to be limitative of the invention. In the example that follows, and throughout the specification, parts are by weight unless otherwise indicated.

EXPERIMENTAL

EXAMPLE

In this example, a computer simulation was conducted employing the process conditions of this invention, wherein FIG. 3 represents the distillation column used in the simulated process. As shown in FIG. 3, column 51, having a top section 94 and a bottom section 95, contains sixty-six trays (vapor-liquid contacting stages) disposed in the column in ascending order from top section 94. Trays (or stages) 1–55 are located above feed stream entry conduit 32 while trays 56–66 are situated below conduit 32.

The impure solution is preheated at heat exchanger 64 to a temperature of from about 50° C. to about 55° C., prior to its introduction into the column 51 at Tray 58. Stripping vapor is introduced to column 51 below Tray 66. An aqueous bottoms product is formed below Tray 66 and has a temperature of about 120° C.–150° C. A portion of the bottoms product is cooled at indirect contact heat exchanger 96 to a temperature of about 55° C. and recycled back as a bottom stream via conduits 57, 100 and 62 to column 51 at Tray 50. There, the bottom stream absorbs the formaldehyde vapor into a liquid phase and water in the bottom stream and the formaldehyde vapor combine to form an apparent azeotrope. The apparent azeotrope travels downward in column 51 and is withdrawn therefrom at conduit 56 and disposed via conduit 57.

The first sidestream (i.e., the acetaldehyde-containing ethylene oxide stream described hereinabove in connection with FIG. 2) is withdrawn from column 51 from Tray 48 via conduit 83. The second sidestream (i.e., the ethylene oxide product stream described hereinabove in connection with FIG. 2) is withdrawn via conduit 85 from above Tray 8.

The simulation showed that the light ends stream in conduit 87 has a formaldehyde content of about 100 ppm by weight arid the ethylene oxide product stream in conduit 85 has a formaldehyde content of about 2–10 ppm by weight.

It will be obvious that various changes and modifications may be made without departing from the invention and it is intended, therefore, that all matter contained in the foregoing description shall be interpreted as illustrative only and not limitative of the invention.

What is claimed is:

1. In a process for recovering ethylene oxide from an aqueous ethylene oxide solution further containing formaldehyde, wherein said aqueous ethylene oxide solution is introduced into a distillation zone as a feed stream and undergoes distillation therein to form an ethylene oxide product sidestream and an aqueous bottoms product, and water is added to the distillation zone to absorb formaldehyde vapor into a liquid phase to form an apparent azeotrope, and removing said apparent azeotrope from said distillation zone, the improvement comprises all or part of said water being a recycled aqueous stream originating from said aqueous bottoms product and introduced to said distillation zone above the feed stream.

2. A process according to claim 1, wherein said recycled aqueous stream is cooled prior to its addition to the distillation zone above the feed stream.

3. A process according to claim 2, wherein said recycled aqueous stream is cooled to a temperature ranging from about 35° C. to about 60° C. prior to its addition to the distillation zone above the feed stream.

4. A process according to claim 1, wherein the recycled aqueous stream is substantially pure water.

5. A process according to claim 1, wherein the ethylene oxide product sidestream comprises up to about 10 parts by weight of formaldehyde per one million parts by weight of said ethylene oxide product sidestream.

6. A process according to claim 5, wherein the ethylene oxide product sidestream comprises from about 2 to about 10 parts by weight of formaldehyde per one million parts by weight of said ethylene oxide product stream.

7. A process according to claim 1, wherein said distillation further produces a light ends stream.

8. A process according to claim 7, wherein said light ends stream comprises up to about 100 parts by weight of formaldehyde per one million parts by weight of said light ends stream.

9. A process according to claim 8, wherein said light ends sidestream comprises up to about 50 parts by weight of formaldehyde per one million parts by weight of said light ends stream.

10. A process according to claim 1, wherein said impure solution is preheated prior to entering said distillation zone.

11. A process according to claim 10, wherein said impure solution is preheated to a temperature ranging from about 35° C. to about 60° C. prior to entering said distillation zone.

12. A process according to claim 1, wherein the impure solution further comprises acetaldehyde.

13. A process according to claim 1, wherein the impure solution further comprises carbon dioxide.

14. A process according to claim 1, wherein the impure solution comprises from about 2% to about 90% by weight of ethylene oxide, from about 10% to about 98% by weight of water, from about 0.001% to about 0.2% by weight of aldehydic impurities, and from 0 up to about 500 parts per million by weight of carbon dioxide.

15. A process according to claim 14, wherein the impure solution comprises from about 40% to about 60% by weight of ethylene oxide, from about 60% to about 40% by weight of water, from about 0.005% to about 0.05% by weight of aldehydic impurities, and from 0 up to about 250 parts per million by weight of carbon dioxide.

16. A process according to claim 14, wherein said aldehydic impurities comprise formaldehyde and acetaldehyde.

17. A process according to claim 16, wherein said impure solution comprises up to about 0.1% by weight of said formaldehyde and from about 0.001% to about 0.1% by weight of said acetaldehyde.

18. A process according to claim 17, wherein said impure solution comprises from about 0.005% to about 0.05% by weight of said formaldehyde and from about 0.002% to about 0.05% by weight of said acetaldehyde.

19. A process according to claim 1, wherein the impure solution comprises a molar ratio of water to ethylene oxide of from about 1:1 to about 50:1.

20. A process according to claim 19, wherein the impure solution comprises a molar ratio of water to ethylene oxide of from about 2:1 to about 30:1.

21. A process according to claim 20, wherein the impure solution comprises a molar ratio of water to ethylene oxide of from about 2:1 to about 4:1.

22. A process according to claim 12, wherein the distillation of said impure solution forms an acetaldehyde-containing ethylene oxide stream.

23. A process according to claim 1, wherein said aqueous bottoms product comprises an aqueous solution containing less than about 0.1 percent by weight of ethylene oxide, less than about 0.1 percent by weight of formaldehyde, less than about 0.001 percent by weight of acetaldehyde, and from about 0.5 to about 20 percent by weight of ethylene glycol.

24. A process according to claim 1, wherein the apparent azeotrope comprises methylene glycol and polyoxymethylenes.

25. A process according to claim 1, wherein said distillation zone is a multi-stage countercurrent distillation zone.

26. A process according to claim 25, wherein said multi-stage countercurrent distillation zone has disposed therein in ascending order above where said aqueous ethylene oxide stream is introduced the following fractionation regions:

(1) a first fractionation region having at least one vapor-liquid contacting stage;

(2) a second fractionation region having at least one vapor-liquid contacting stage;

(3) a third fractionation region having at least five vapor-liquid contacting stages; and (4) a fourth fractionation region having at least one vapor-liquid contacting stage;

said multi-stage, countercurrent distillation zone having disposed therein below said feed stream a fifth fractionation region having at least one vapor-liquid contacting stage;

each of said fractionation regions having means for providing countercurrent contact between downflowing liquid and upwardly flowing vapor.

27. A process according to claim 26, wherein each vapor-liquid contacting stage is a tray selected from the group consisting of sieve trays, bubble cap trays, valve trays, and tunnel cap trays.

28. A process according to claim 27, wherein one or more of said fractionation regions comprises packings which are substantially inert to vapor and liquid.

29. A process according to claim 26, wherein the impure solution further comprises acetaldehyde.

* * * * *